(12) United States Patent
Oka et al.

(10) Patent No.: US 7,820,625 B2
(45) Date of Patent: Oct. 26, 2010

(54) UV-INDUCED DERMATITIS INHIBITOR AND ATOPIC DERMATITIS INHIBITOR

(75) Inventors: Syuichi Oka, Tsukuba (JP); Akinori Tsuruda, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 340 days.

(21) Appl. No.: 11/887,766

(22) PCT Filed: Mar. 27, 2006

(86) PCT No.: PCT/JP2006/306184

§ 371 (c)(1),
(2), (4) Date: Oct. 3, 2007

(87) PCT Pub. No.: WO2006/106633

PCT Pub. Date: Oct. 12, 2006

(65) Prior Publication Data

US 2009/0215702 A1    Aug. 27, 2009

(30) Foreign Application Priority Data

| Apr. 4, 2005 | (JP) | ............................. 2005-107827 |
| Sep. 30, 2005 | (JP) | ............................. 2005-286163 |
| Feb. 16, 2006 | (JP) | ............................. 2006-039285 |

(51) Int. Cl.
*A61K 38/06* (2006.01)
*A61K 38/07* (2006.01)
*A61K 38/08* (2006.01)

(52) U.S. Cl. ......................................... 514/17; 514/18
(58) Field of Classification Search ...................... None
See application file for complete search history.

(56) References Cited

U.S. PATENT DOCUMENTS

| 6,262,021 | B1 * | 7/2001 | Uvnas-Moberg et al. ...... 514/11 |
| 2005/0119274 | A1 | 6/2005 | Evenou et al. |
| 2007/0213276 | A1 * | 9/2007 | Oka et al. ..................... 514/17 |

FOREIGN PATENT DOCUMENTS

| EP | 1 132 396 | 9/2001 |
| JP | 2000-309521 | 11/2000 |
| JP | 2003-137807 | 5/2003 |
| JP | 2004-505078 | 2/2004 |
| WO | 92/04373 | 3/1992 |
| WO | 00/29425 | 5/2000 |
| WO | 02/10158 | 2/2002 |
| WO | 03/082859 | 10/2003 |
| WO | 2005/095441 | 10/2005 |

OTHER PUBLICATIONS

International Search Report issued in the International (PCT) Application of which the present application is the U.S. National Stage.
A. Tsuruda et al., "A Short Peptide GPIGS Promotes Proliferation of Hair Bulb Keratinocytes and Accelerates Hair regrowth in Mice", Biol. Pharm. Bull., vol. 28, No. 3, pp. 485-489, 2005.

* cited by examiner

*Primary Examiner*—Jeffrey E Russel
(74) *Attorney, Agent, or Firm*—Wenderoth, Lind & Ponack, L.L.P.

(57) ABSTRACT

At least one substance selected from the group consisting of a water-soluble peptide comprising at least one unit selected from the group consisting of an isoleucylglycylseryl unit, a prolylisoleucylglycylseryl [SEQ ID NO: 2] unit, a glycylprolylisoleucylglycylseryl [SEQ ID NO: 6] unit, a glycylprolylisoleucylglycylthreonyl [SEQ ID NO: 7] unit, a prolylisoleucylglycyl unit and a glycylprolylisoleucylglycyl [SEQ ID NO: 1] unit and a water-soluble salt thereof can be used as an UV-induced dermatitis inhibitor or atopic dermatitis inhibitor.

11 Claims, 3 Drawing Sheets

| Days after UVB irradiation (Days) | Amount of water evaporation (g/m²/hr) | | | |
|---|---|---|---|---|
| | (5-1) | (5-2) | (5-3) | (5-4) |
| 1 | 5.0 | 8.3 | 7.1 | 7.0 |
| 2 | 5.0 | 8.9 | 8.5 | 9.1 |
| 3 | 4.0 | 13.3 | 12.7 | 10.2 |
| 4 | 4.4 | 28.0 | 23.5 | 22.7 |
| 5 | 4.4 | 30.1 | 30.2 | 18.3 |
| 6 | 4.5 | 45.7 | 35.8 | 24.5 |
| 7 | 3.2 | 38.4 | 30.2 | 18.5 |
| 8 | 5.2 | 21.9 | 17.7 | 13.5 |
| 9 | 5.6 | 13.8 | 11.4 | 10.1 |
| 10 | 6.2 | 9.6 | 10.1 | 8.1 |
| Total | 47.4 | 217.9 | 187.3 | 141.9 |
| Rate of increase (%) | 0.0 | 100.0 | 82.1 | 55.4 |

SEQUENCE LISTING

<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: Sythetic Construct; Chemical Synthesis

<400> SEQUENCE: 1

Gly Pro Ile Gly
1

<210> SEQ ID NO 2
<211> LENGTH: 4
<212> TYPE: PRT
<213> ORGANISM: Artificial Sequence
<220> FEATURE:
<223> OTHER INFORMATION: Sythetic Construct; Chemical Synthesis

<400> SEQUENCE: 2

Pro Ile Gly Ser
1

<210> SEQ ID NO 3
<211> LENGTH: 6
<212> TYPE: PRT

```
<213> ORGANISM: Artificial Sequence
<220> FEATURE:
<223> OTHER INFORMATION: Sythetic Construct; Chemical Synthesis

<400> SEQUENCE: 3

Ala Gly Pro Ile Gly Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Sythetic Construct; Chemical Synthesis

<400> SEQUENCE: 4

Ser Gly Pro Ile Gly Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Sythetic Construct; Chemical Synthesis

<400> SEQUENCE: 5

Gly Ser Gly Pro Ile Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Sythetic Construct; Chemical Synthesis

<400> SEQUENCE: 6

Gly Pro Ile Gly Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Sythetic Construct; Chemical Synthesis

<400> SEQUENCE: 7

Gly Pro Ile Gly Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Sythetic Construct; Chemical Synthesis
<220> FEATURE:
<221> NAME/KEY: MISC_FEATURE
<222> LOCATION: (5)..(5)
<223> OTHER INFORMATION: Xaa is a hydroxyl group-containing amino acid

<400> SEQUENCE: 8

Gly Pro Ile Gly Xaa
1               5
```

UV-INDUCED DERMATITIS INHIBITOR AND ATOPIC DERMATITIS INHIBITOR

This application is a U.S. national stage of International Application No. PCT/JP2006/306184 filed Mar. 27, 2006.

TECHNICAL FIELD

The present invention relates to a UV-induced dermatitis inhibitor and an atopic dermatitis inhibitor.

BACKGROUND ART

Heretofore, an external preparation for skin for anti-aging consisting of a polymerization product with an average molecular weight of 280-20000 of a tripeptide composed of one glycine residue and two other amino acid residues in a degradation product of collagen or gelatin by collagenase (see Patent Document 1), a collagen-production promoter comprising a mixture of tripeptides (Gly-Ala-Arg), (Gly-Ala-Hyp), (Gly-Ala-Lys), (Gly-Pro-Ala), (Gly-Pro-Arg), (Gly-Pro-Hyp), and (Gly-Pro-Ser) as an active ingredient (see Patent Document 2) and others are known as physiologically active substances comprising an oligopeptide or a polymerization product thereof as an active ingredient.

Alternatively, an oral hair growth promoting agent comprising, as an active ingredient, a peptide represented by $R^1$-Met-Ile-X$R^2$ (wherein X represents Trp, Phe, Trp-Leu, Phe-Leu, Tyr-Leu, Ile-Leu, or Leu-Leu; $R^1$ represents a hydrogen atom or an amino-protecting group; and $R^2$ represents a hydroxyl- or carboxyl-protecting group) or a pharmacologically acceptable salt thereof is known as a special substance (see Patent Document 3).

A variety of physiologically active substances comprising a peptide as an active ingredient is known, as described above. However, a UV-induced dermatitis inhibitor and an atopic dermatitis inhibitor comprising a peptide as an active ingredient are unknown.

Patent Document 1: Japanese Patent Laid-Open No. 2000-309521

Patent Document 2: Japanese Patent Laid-Open No. 2003-137807

Patent Document 3: Pamphlet of International Publication No. WO 00/29425

DISCLOSURE OF THE INVENTION

An object of the present invention is to provide a UV-induced dermatitis inhibitor and an atopic dermatitis inhibitor using a peptide.

Means to Solve the Problems

The inventors have conducted diligent studies on the aforementioned problems and have consequently found that the aforementioned object can be attained by the following means.

(1) A UV-induced dermatitis inhibitor comprising at least one member selected from the group consisting of: water-soluble peptides comprising at least one unit selected from the group consisting of an isoleucylglycylseryl unit, a prolylisoleucylglycylseryl [SEQ ID NO: 2] unit, a glycylprolylisoleucylglycylseryl [SEQ ID NO: 6] unit, a glycylprolylisoleucylglycylthreonyl [SEQ ID NO: 7] unit, a prolylisoleucylglycyl unit, and a glycylprolylisoleucylglycyl [SEQ ID NO: 1] unit; and water-soluble salts thereof.

(2) A UV-induced dermatitis inhibitor comprising at least one member selected from the group consisting of: water-soluble peptides comprising at least one unit selected from the group consisting of an isoleucylglycylseryl unit, a prolylisoleucylglycyl unit, and a glycylprolylisoleucylglycylseryl [SEQ ID NO: 6] unit; and water-soluble salts thereof.

(3) A UV-induced dermatitis inhibitor comprising at least one member selected from the group consisting of: water-soluble peptides comprising an isoleucylglycylseryl unit and/or a prolylisoleucylglycyl unit; and water-soluble salts thereof.

(4) A UV-induced dermatitis inhibitor comprising at least one member selected from the group consisting of: water-soluble peptides comprising an isoleucylglycylseryl unit; and water-soluble salts thereof.

(5) A UV-induced dermatitis inhibitor comprising at least one member selected from the group consisting of water-soluble peptides represented by the following formula (1) and water-soluble salts thereof:

Gly-Pro-Ile-Gly-X[SEQ ID NO:8]   Formula (1)

[in the formula (1), X denotes a hydroxyl group-containing amino acid unit].

(6) The UV-induced dermatitis inhibitor according to (5), wherein X in the above-given formula (1) denotes Ser or Thr.

(7) The UV-induced dermatitis inhibitor according to any one of (1) to (6), wherein the aforementioned water-soluble peptide is derived from 3 to 8 amino acids.

(8) An atopic dermatitis inhibitor comprising at least one member selected from the group consisting of: water-soluble peptides comprising at least one unit selected from the group consisting of an isoleucylglycylseryl unit, a prolylisoleucylglycylseryl [SEQ ID NO: 2] unit, a glycylprolylisoleucylglycylseryl [SEQ ID NO: 6] unit, a glycylprolylisoleucylglycylthreonyl [SEQ ID NO: 7] unit, a prolylisoleucylglycyl unit, and a glycylprolylisoleucylglycyl [SEQ ID NO: 1] unit; and water-soluble salts thereof.

(9) An atopic dermatitis inhibitor which is a solution comprising at least one member selected from the group consisting of water-soluble peptides represented by the following formula (1) and water-soluble salts thereof in a concentration of 3 mg/ml or higher:

Gly-Pro-Ile-Gly-X[SEQ ID NO:8]   Formula (1)

[in the formula (1), X denotes a hydroxyl group-containing amino acid unit].

(10) The atopic dermatitis inhibitor according to (8) which is an ointment.

(11) The atopic dermatitis inhibitor according to (8) which is in a solid form.

ADVANTAGE OF THE INVENTION

A water-soluble tripeptide or tetrapeptide and a water-soluble salt thereof as well as a water-soluble peptide represented by the formula (1) and a water-soluble salt thereof used in the present invention have an excellent moisture retention property. Therefore, they can be used preferably, in addition to the purposes described above, for preventing dry eyes and can enhance the feeling of use of cosmetics and the like when utilized in the cosmetics and the like. Furthermore, they can be utilized as an external preparation for skin using these effects in combination with the effects of a UV-induced dermatitis inhibitor and an atopic dermatitis inhibitor.

BEST MODE FOR CARRYING OUT THE INVENTION

Hereinafter, the contents of the present invention will be described in detail. In the present specification, the symbol "-" used for denoting a numerical range means that numerical values described before and after the symbol are included as lower and upper limits, respectively.

(Peptide)

A peptide that can be used in the present invention is a water-soluble peptide (hereinafter, also referred to as a "peptide of the present invention") comprising at least one unit selected from the group consisting of an isoleucylglycylseryl unit, a prolylisoleucylglycylseryl [SEQ ID NO: 2] unit, a glycylprolylisoleucylglycylseryl [SEQ ID NO: 6] unit, a glycylprolylisoleucylglycylthreonyl [SEQ ID NO: 7] unit, a prolylisoleucylglycyl unit, and a glycylprolylisoleucylglycyl [SEQ ID NO: 1] unit.

The peptide of the present invention is, preferably, a water-soluble peptide comprising at least one unit selected from the group consisting of an isoleucylglycylseryl unit, a prolylisoleucylglycyl unit (more preferably, a prolylisoleucylglycylseryl [SEQ ID NO: 2] unit), and a glycylprolylisoleucylglycylseryl [SEQ ID NO: 6] unit.

The peptide of the present invention is, more preferably, a water-soluble peptide comprising a prolylisoleucylglycyl unit and/or an isoleucylglycylseryl unit.

The peptide of the present invention is, still more preferably, a water-soluble peptide comprising an isoleucylglycylseryl unit.

The peptide of the present invention may be an oligopeptide derived from approximately 3-10 amino acids or may be a polypeptide derived from 10 or more amino acids. The peptide of the present invention is derived from, preferably, 3-8 amino acids, more preferably, 3-7 amino acids and, still more preferably, 3-5 amino acids.

The tripeptide of the present invention is, preferably, isoleucylglycylserine or prolylisoleucylglycine.

The tetrapeptide of the present invention is, preferably, a water-soluble peptide comprising the aforementioned tripeptide bound before or after it with an amino acid residue. In this context, examples of preferable amino acid residues include glycyl, alanyl, arginyl, asparagyl, lysyl, seryl, threonyl, valyl, and glutamyl groups.

The tetrapeptide of the present invention is, more preferably, glycylprolylisoleucylglycine (SEQ ID NO: 1) or prolylisoleucylglycylserine (SEQ ID NO: 2).

The oligopeptide of the present invention is, preferably, a water-soluble peptide comprising the aforementioned tripeptide (e.g., isoleucylglycylserine) bound before and/or after it with 2 or more amino acid residues in total. In this context, examples of preferable amino acid residues can include the same amino acid residues as described for the tetrapeptide.

The oligopeptide of the present invention is, more preferably, a water-soluble peptide comprising glycylprolylisoleucylglycine [SEQ ID NO: 1] or prolylisoleucylglycylserine [SEQ ID NO: 2] before or after it with an amino acid residue. In this context, examples of the amino acid residue can include the same amino acid residues as described for the tetrapeptide.

Another preferable example of the oligopeptide of the present invention includes a water-soluble peptide comprising a water-soluble peptide represented by the following formula (1):

Gly-Pro-Ile-Gly-X[SEQ ID NO:8]　　　　Formula (1)

[in the formula (1), X denotes a hydroxyl group-containing amino acid unit].

In this context, X is, preferably, Ser or Thr or, more preferably, Ser.

The oligopeptide of the present invention is, still more preferably, an oligopeptide consisting of only the water-soluble peptide represented by the above-given formula (1) or an oligopeptide having, at the carboxyl terminus, the pentapeptide unit of the water-soluble peptide represented by the above-given formula (1).

Such oligopeptides are exemplified by alanylglycylprolylisoleucylglycylserine (SEQ ID NO: 3), serylglycylprolylisoleucylglycylserine (SEQ ID NO: 4), glycylserylglycylprolylisoleucylglycylserine (SEQ ID NO: 5) and the like.

The polypeptide of the present invention is, preferably, a peptide comprising the tripeptide, tetrapeptide, or oligopeptide exemplified above. Alternatively, preferred is a polypeptide comprising the water-soluble peptide represented by the formula (1), of which a polypeptide comprising at least one of alanylglycylprolylisoleucylglycylserine [SEQ ID NO: 3], serylglycylprolylisoleucylglycylserine [SEQ ID NO: 4], and glycylserylglycylprolylisoleucylglycylserine [SEQ ID NO: 5] is more preferred.

The polypeptide of the present invention has a molecular weight of, preferably, 500 or smaller or, more preferably, 450 or smaller in respect of the higher water solubility.

In the present invention, a peptide in a free form or water-soluble salts of the peptides described above may be used. Examples of the water-soluble salts include sodium salts, potassium salts, lithium salts, and ammonium salts.

The peptide that can be used in the present invention can be produced by reacting a raw material amino acid having a protected α-amino group with an amino acid having a protected carboxyl group by a routine method for forming a peptide bond in peptide synthesis such as, for example, a condensation method, active esterification method, azide method, or mixed acid anhydride method, and thereby forming a peptide, which in turn is repeatedly subjected to the step of eliminating the protecting groups.

This condensation method is the most general method for forming a peptide bond. In this method, for example, dicyclohexylcarbodiimide (DCC), diisopropylcarbodiimide (DIPC), N-ethyl-N'-3-dimethylaminopro-pylcarbodiimide (WSCI) and hydrochloride thereof (WSCI.HCl), benzotriazol-1-yl-tris(dimethylamino)phosphonium hexafluorophosphide (BOP), and diphenylphosphoryl diazide (DPPA) can be used as a condensing agent either alone or in combination with N-hydroxysuccinimide (HONSu), 1-hydroxybenzotriazole (HOBt), or 3-hydroxy-4-oxo-3,4-dihydro-1,2,3-benzotriazine (HOObt).

In the active esterification method, for example, p-nitrophenyl ester (ONp), N-hydroxysuccinimide ester (ONSu), or pentafluorophenyl ester (OPfp) can be used as the active ester.

The azide method is a method in which an amino acid or peptide is reacted with anhydrous hydrazine to form a corresponding hydrazide, and is known as a segment condensation method with low racemization.

Furthermore, the mixed acid anhydride method is a method in which isobutyloxycarbonylchloride, diethylacetyl chloride, trimethylacetyl chloride, or the like is used to form a mixed anhydride of the carboxyl group of an amino acid, and is advantageous since this method can strongly activate the carboxyl group at low temperatures.

On the other hand, those easily eliminated by acid treatment, hydrolysis, or catalytic reduction are used as protecting groups for an amino acid. Among such protecting groups, α-amino-protecting groups include benzyloxycarbonyl, tert-butoxycarbonyl, 9-fluorenylmethoxycarbonyl, 3-nitro-2-pyridinesulfenyl and methoxybenzyloxycarbonyl groups and the like. The protection of a carboxyl group is performed by forming methyl ester, ethyl ester, benzyl ester, tert-butyl ester, phenacyl ester, or the like.

In the case of an α-amino acid having a hydroxyl group at the side chain, this hydroxyl group has to be protected. The protecting group is suitably a benzyl group that is easily eliminated by catalytic reduction with a platinum black catalyst or by strong acid treatment or a tert-butyl group that is easily eliminated by weak acid treatment.

Such an α-amino acid ester or a raw material amino acid with the amino or hydroxyl group protected is easily obtained as a commercially available product.

The preparation of the peptide that can be used in the present invention can be performed by both of a liquid phase method wherein a raw material amino acid or a derivative thereof is evenly dissolved and reacted in a solvent and a solid phase method wherein a peptide chain is extended on an insoluble resin, and is advantageously performed by a method using an automatic solid-phase synthesizer. According to this method, a desired oligopeptide can be obtained in a short time and in a high purity.

The peptide that can be used in the present invention is sometimes obtained as a racemic body and can also be obtained, if desired, as an optically active substance by subjecting the racemic body to optical resolution by any routine method. This optical resolution can be performed by a method in which a diastereomer formed between the racemic amino acid and an appropriate optically active substance is subjected to fractional crystallization, a method using an enzyme, or a method performed by high-performance liquid chromatography using a chiral carrier.

The peptide of the present invention is soluble in water or alcohols. This peptide can be identified by mass spectrometry, an infrared absorption spectrum, or high-performance liquid chromatography (HPLC).

A UV-induced dermatitis inhibitor described in the present invention refers to an agent that plays a role, for example, in inhibiting and preventing skin inflammation attributed to UV irradiation, inhibiting wrinkles or flecks associated therewith, and skin lightening. In skin exposed to a large dose of UV, it is known that inflammation occurs in the structure of the stratum corneum, leading to reduction in the barrier function of keratin. In such skin, conditions appear, such as varicella, suntan, and sunburn as acute UV-induced symptoms and wrinkles, sagging, flecks, and reduction in elasticity as chronic UV-induced symptoms. The use of the UV-induced dermatitis inhibitor of the present invention can inhibit these conditions.

An atopic dermatitis inhibitor described in the present invention refers to an agent that plays a role, for example, in inhibiting and preventing atopic dermatitis, alleviating itching associated therewith, and improving dry skin. Contact dermatitis is also included as the targets of the atopic dermatitis inhibitor of the present invention. Atopic dermatitis causes a damaged state in the barrier function of keratin. It has been pointed out that such skin becomes so-called sensitive skins and develops inflammation even by a slight external stimulation, leading to further deterioration in the disease conditions. Thus, the use of the atopic dermatitis inhibitor of the present invention can inhibit these conditions.

The UV-induced dermatitis inhibitor or the atopic dermatitis inhibitor of the present invention can be prepared and used as cosmetics and cosmeceuticals such as skin lotions, creams, milky lotions, foundations, oil-based cosmetics, packs, skin washes, spray agents, aerosol agents and the like or as external preparations such as ointments, liniments, lotions, emulsions and the like.

The aforementioned external preparations can be produced by the addition of pharmacologically and pharmaceutically acceptable additives. Examples of the pharmacologically and pharmaceutically acceptable additives can include, for example, excipients, disintegrants or disintegration aids, binders, lubricants, coating agents, pigments, diluents, bases, solvents or solubilizing agents, isotonization agents, pH adjusters, stabilizers, propellants, adhesives and the like. The aforementioned external preparations may be supplemented with one or two or more of other UV-induced dermatitis inhibitors or atopic dermatitis inhibitors without departing from the scope of the present invention. An administration method for the UV-induced dermatitis inhibitor or the atopic dermatitis inhibitor of the present invention is not particularly limited and is, preferably, an external preparation for skin. A dose of the external preparation of the present invention is not particularly limited and can be selected appropriately according to the types of an active ingredient, and so on. Furthermore, the dose can be increased or decreased appropriately according to various factors to be usually considered, such as the body weight and age of the patient, the type and conditions of disease, an administration route and the like. For UV-induced dermatitis inhibitor use, the UV-induced dermatitis inhibitor can usually be used at a dose ranging from 0.00001-1000 mg or, preferably, 0.001-10 mg, per day for adults. For atopic dermatitis inhibitor use, the atopic dermatitis inhibitor can usually be used at a dose ranging from 0.00001-1000 mg or, preferably, 0.001-10 mg, per day for adults.

The UV-induced dermatitis inhibitor and the atopic dermatitis inhibitor of the present invention are repetitively applied for use, for example, approximately once to five times a day, to the affected part.

The UV-induced dermatitis inhibitor and the atopic dermatitis inhibitor of the present invention may further contain a variety of vehicles and additives usually used in pharmaceutical drugs or quasi-drugs, cosmetics, and so on. Examples of various vehicles include a variety of carriers, extenders, diluents, expanders, dispersants, excipients, binder solvents, solubilizing agents, buffers, dissolution promoters, gelling agents, suspending agents, milk proteins, collagen, rice bran oil, lecithin and the like. Examples of the additives include vitamins, organic acids, colorants, flavors, anti-humidity agents, fibers, electrolytes, minerals, nutrients, antioxidants, preservatives, aromatics, humectants, natural plant extracts, coffee extracts, fruit extracts, vegetable extracts and the like.

When the UV-induced dermatitis inhibitor of the present invention is prepared in a liquid form, the UV-induced dermatitis inhibitor is dissolved, preferably, in a concentration of 0.001 mg/ml or higher, more preferably in a concentration of 0.1 mg/ml or higher, still more preferably in a concentration of 1 mg/ml or higher, still further more preferably in a concentration of 3 mg/ml or higher or, most preferably in a concentration of 10 mg/ml or higher, in an aqueous medium.

When the atopic dermatitis inhibitor of the present invention is prepared in a liquid form, the atopic dermatitis inhibitor is dissolved, preferably, in a concentration of 0.001 mg/ml or higher, more preferably in a concentration of 0.1 mg/ml or higher, still more preferably in a concentration of 1 mg/ml or higher, still more preferably in a concentration of 3 mg/ml or higher or, most preferably in a concentration of 10 mg/ml or higher, in an aqueous medium.

The aqueous medium used in this procedure is, preferably, a mixed solvent of water and a water-soluble organic solvent.

Examples of the water-soluble organic solvent include: alcohols such as ethyl alcohol; polyhydric alcohols such as ethylene glycol, diethylene glycol, dipropylene glycol, glycerin, and 1,3-butylene glycol; polar organic solvents such as dimethylformamide and dimethyl sulfoxide and others. These solvents may be used singly or can be used as a combination of two kinds or more of them. A preferable water-soluble solvent is a mixed solvent of water, propylene glycol, and ethyl alcohol.

When the UV-induced dermatitis inhibitor and the atopic dermatitis inhibitor of the present invention are prepared into ointments, hydrophobic bases (oleaginous bases) or hydrogel bases are preferably used.

Fats and oils, waxes, hydrocarbons, and the like are used as hydrophobic bases (oleaginous base). Specific examples thereof include: mineral bases such as yellow petrolatum, white petrolatum, paraffin, liquid paraffin, plastibase, silicones and others; and animal and plant bases such as beeswax, animal and plant fats and oils and others.

Examples of the hydrogel bases include carboxyvinyl polymers, gel bases, fat-free ointments, polyethylene glycols and others.

When the UV-induced dermatitis inhibitor and the atopic dermatitis inhibitor of the present invention are prepared into emulsion bases, oil-in-water bases such as hydrophilic ointments, vanishing creams and the like and water-in-oil bases such as hydrophilic petrolatum, purified lanolin, hydrous lanolin, cold creams, hydrophilic plastibase and the like can be used as the bases.

When the UV-induced dermatitis inhibitor and the atopic dermatitis inhibitor of the present invention are prepared into suspension bases, lotions and FAPG (Fatty alcohol-propylene glycol) bases, that is, lyogel bases containing fine particles such as stearyl alcohol or cetyl alcohol suspended in propylene glycol can be used as the bases.

When the UV-induced dermatitis inhibitor and the atopic dermatitis inhibitor of the present invention are prepared into creams, cera alba, liquid paraffin, lanolin, paraffin, petrolatum, spermaceti, sorbitan sesquioleate, glycerin monostearate, sorbitan monostearate, glycerin, propylene glycol, carboxyvinyl polymers and the like can be used as the bases.

When the UV-induced dermatitis inhibitor and the atopic dermatitis inhibitor of the present invention are prepared into bases for oil solutions, for example, liquid paraffin, lanolin, squalane, vegetable oils, isopropyl myristate, isopropyl palmitate, glycerin monoisostearate monomyristate, tridecyl isononanoate, neopentyl glycol dicaprate, glycerin tri-2-ethylhexanoate, octyldodecyl lactate, and diglyceryl triisostearate can be used as the bases.

When the UV-induced dermatitis inhibitor and the atopic dermatitis inhibitor of the present invention are prepared into liniments, for example, glycerin and carmellose sodium can be used as the bases.

Emulsions and creams contain an insoluble solution as small droplets dispersed in a liquid dispersion medium. They can be produced by adding an active ingredient, an emulsifier, and the like into a liquid dispersion medium and mixing the mixture by stirring with a homogenizer or colloid mill. For the emulsifier, for example, a medicated soap, stearic acid triethanolamine, sodium lauryl sulfate, sorbitan sesquioleate, polysorbates, polyoxyl 40 stearate, lauromacrogol, cholesterol, lecithin, gum arabic, and gelatin can be used as the bases.

Oil solutions are oily and slurry external preparations and are usually produced by dissolving or suspending an active ingredient in an oily base.

Lotions are preparations containing an active ingredient dispersed finely and evenly in an aqueous solution and are classified into suspension lotions and emulsion lotions. For example, gum arabic, sodium alginate, CMC-Na, and methyl cellulose are used as suspending agents. The emulsifiers described above are used as emulsifiers.

EXAMPLES

Hereinafter, the present invention will be described more specifically with reference to Examples. Materials, used amounts, proportions, the contents and procedures of operation, and so on shown in Examples below can be modified appropriately without departing the scope of the present invention. Thus, the scope of the present invention is not intended to be limited to specific examples shown below.

Example 1

Preparation of Test Substances

A 1 mg portion of glycylprolylisoleucylglycylserine (SEQ ID NO: 6) (hereinafter, also referred to as "GPIGS") (manufactured by AMERICAN PEPTIDE COMPANY, Inc., lot. CC-09-119) was weighed. This GPIGS [SEQ ID NO: 6] was dissolved by the addition of 300 µl of Otsuka distilled water for injection (manufactured by Otsuka Pharmaceutical Co., Ltd., cat. 322134). Then, this solution was mixed with 200 µl of propylene glycol (manufactured by Wako Pure Chemical Industries, Ltd., cat. 161-05006) and 500 µl of ethanol (manufactured by Wako Pure Chemical Industries, Ltd., cat. 057-00456) to prepare 1 mg/ml GPIGS [SEQ ID NO: 6] solution (1).

Preparation of Sample

Seven-week-old mice (produced by Japan SLC. Inc, BALB/c line) were raised for 1 week and acclimatized.

A 10 µl portion (14.5 mg) of 2,4-ditrifluorobenzene (manufactured by NACALAI TESQUE, INC., cat. 135-12) (DNFB) was added to 9.7 ml of (acetone:olive oil=3:1) solution to prepare 1.5 mg/ml DNFB solution.

Induction of Dermatitis

A 25 µl portion of 1.5 mg/ml DNFB solution was applied five times (once a week) to each of the front and back sides of the left and right earlobes of the BALB/c mice (8-week-old).

From one day after the 4th DNFB solution application, 25 µl of the drug solution was applied once a day to each of the front and back sides of the left and right earlobes (in the 5th DNFB solution application, the GPIGS [SEQ ID NO: 6] solution (1) was applied 1 hour before DNFB application). Forty-eight hours after the 5th DNFB solution application, an amount of water evaporation in the auricle surfaces was measured with Tewameter TM300 (manufactured by Courage+ Khazaka electronic GmbH.) to evaluate the barrier function of keratin (1-3) (the present invention).

The barrier function of keratin was also evaluated on (1-1) wherein the same procedures aforementioned were performed except that a (acetone:olive oil=3:1) solution was applied instead of the DNFB solution and (1-2) (Comparative Example) wherein the same procedures aforementioned were performed except that a solution containing the GPIGS [SEQ ID NO: 6] solution (1) except for GPIGS [SEQ ID NO: 6] was used.

All the experiments were conducted using five mice.

Figure 1:
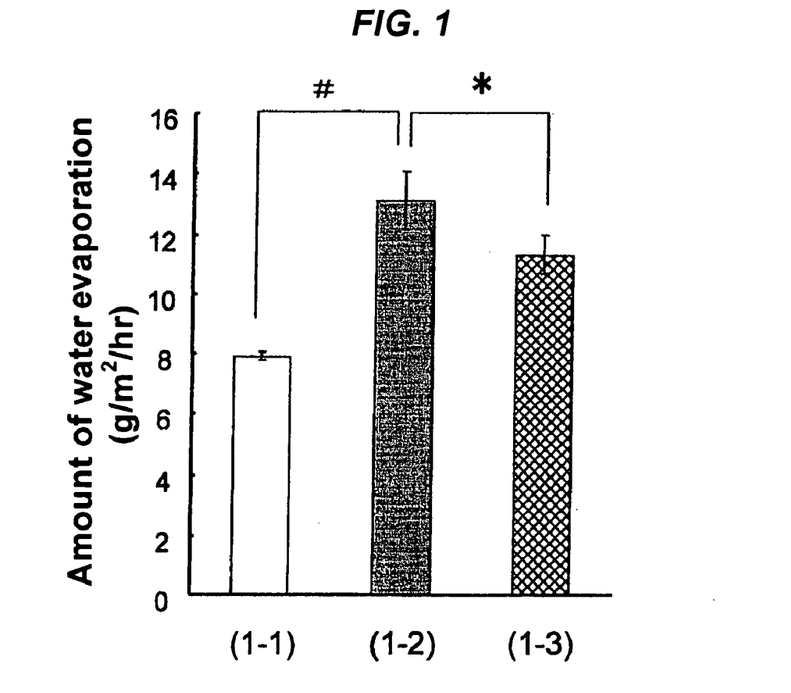
FIG. 1 is a graph showing an amount of water evaporation when a pentapeptide is applied to inflammatory skin.

The results are shown in FIG. 1. The data in FIG. 1 are indicated with mean±standard deviation (mean±S.E.). Statistical analysis was conducted by Student's t-test (Stat View J-4.02, Abacus Concepts Inc.). A significant level less than 5% (p<0.05) means that a significant difference is present. In this context, the amount of water evaporation of (1-2) was 13.11 g/m$^2$/hr and was significantly larger than that of (1-1) (7.91 g/m$^2$/hr). This could demonstrate that the barrier function of keratin was remarkably reduced in the mouse skin to which the DNFB solution was applied. The amount of water evaporation of (1-3) (the present invention) was 11.30 g/m$^2$/hr and was significantly smaller than that of (1-2) (Comparative Example). This demonstrated that GPIGS [SEQ ID NO: 6] exhibited an improving effect on the barrier function of keratin damaged by dermatitis.

Example 2

The same experiment as in Example 1 was conducted except that the concentration of the GPIGS [SEQ ID NO: 6] solution (1) was set to 3 mg/ml. As a result, more excellent barrier function of keratin than that in Example 1 was observed.

Example 3

Preparation of Test Substance

A GPIGS [SEQ ID NO: 6] solution (1) was prepared in the same way as in Example 1.

Preparation of Sample

Mice used were 10-week-old mice (produced by Japan SLC. Inc, Hos:HR-1 line) raised for 1 week or longer in the breeding room of National Institute of Advanced Industrial Science and Technology and acclimatized.

The backs of the mice fixed under pentobarbital anesthesia were irradiated with 150 mJ/cm$^2$ UVB for 5 days (once a day) to cause skin damage. A 100 µl portion of the drug solution was applied once a day immediately after UVB irradiation to each of the skin surfaces of the backs. An amount of water evaporation in the skin surfaces of the backs was measured with Tewameter TM300 (manufactured by Courage+ Khazaka electronic GmbH.) to evaluate the barrier function of keratin.

All the experiments were conducted using four mice.

Figure 2:
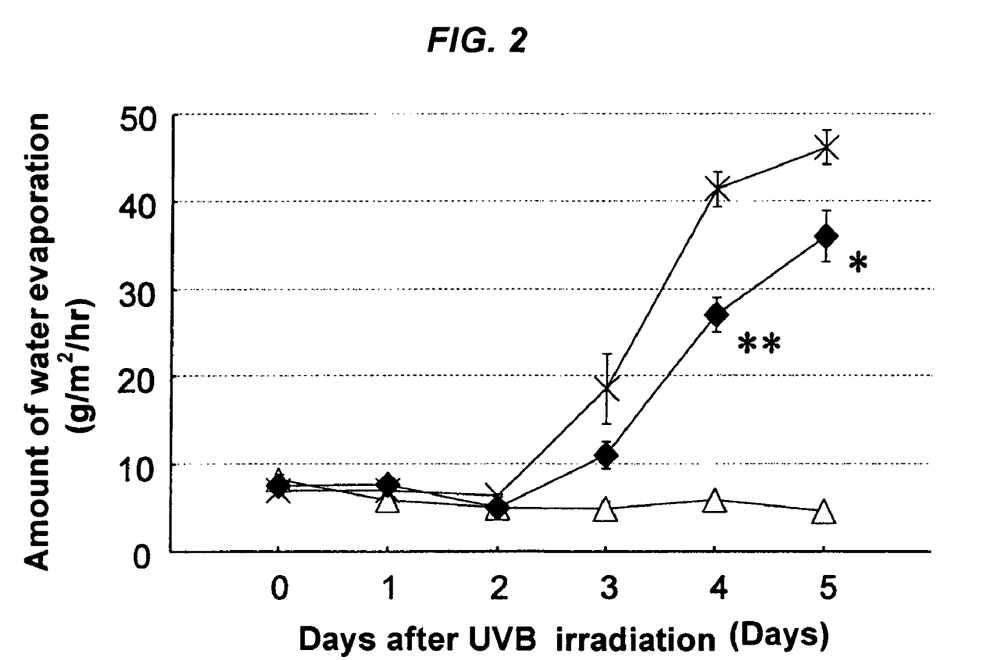
FIG. 2 is a graph showing an amount of water evaporation when a pentapeptide is applied to UV-irradiated skin.

The results are shown in FIG. 2. The data in FIG. 2 are indicated with mean±standard deviation (mean±S.E.). Statistical analysis was conducted by Student's t-test (Stat View J-4.02, Abacus Concepts Inc.). A significant level less than 5% (p<0.05) means that a significant difference is present. In this context, the open triangle denotes (2-1) without UVB irradiation; x denotes (2-2) (Comparative Example) using a solution containing the GPIGS [SEQ ID NO: 6] solution (1) except for GPIGS [SEQ ID NO: 6]; and the solid diamond denotes Example of the present application (2-3).

Both the amounts of water evaporation of (2-2) and (2-3) were increased due to continuous UVB irradiation as the day went on. However, the rate of this increase was lower in (2-3) (the present invention) than in (2-2) (Comparative Example). Particularly, the amount of water evaporation of (2-3) (the present invention) following the fourth day after UVB irradiation was significantly lower than that of (2-2) (Comparative Example). This demonstrated that GPIGS [SEQ ID NO: 6] exhibited an improving effect on the barrier function of keratin damaged by UVB irradiation.

Example 4

A 1.0 g portion of Hiviswako 104 (manufactured by Wako Pure Chemical Industries, Ltd.), 20.0 g of propylene glycol, 1.1 g of diisopropanolamine, 1.0 g of gentamycin solution, and 76.7 g of purified water were added to 10 mg of GPIGS [SEQ ID NO: 6] and mixed to prepare an ointment. This ointment was applied to mice treated in the same way as in Examples 1 and 2. As a result, improvement in the dermatitis of each mouse was observed.

Example 5

A 100 mg portion of Hiviswako 104 (manufactured by Wako Pure Chemical Industries, Ltd.), 7.8 ml of Otsuka distilled water for injection, 2 ml of ethanol, 50 µl of 1 N HCl, and 50 µl of 5 M NaOH were added to 10 mg or 30 mg of GPIGS and mixed together to prepare two kinds of ointments in concentrations of 1 mg/ml and 3 mg/ml [(3-3) and (3-4) in this order]. These ointments were separately applied to mice treated in the same way as in Example 1. The results are shown in FIG. 3.

Figure 3:
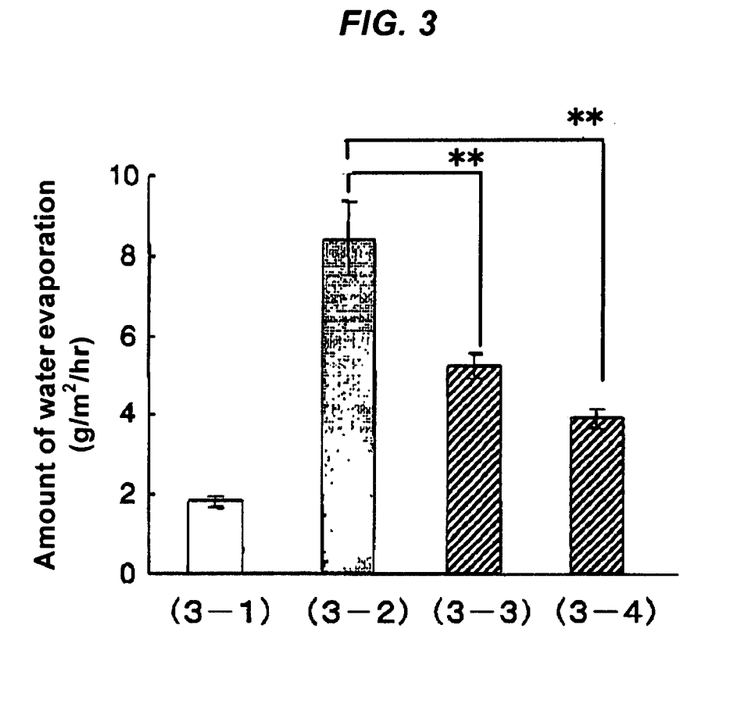
FIG. 3 is a graph showing an amount of water evaporation when an ointment of a pentapeptide is applied to inflammatory skin.

In FIG. 3, (3-3) denotes a group to which 1 mg/ml GPIGS [SEQ ID NO: 6] ointment (3-3) was applied; (3-4) denotes a group to which 3 mg/ml GPIGS [SEQ ID NO: 6] ointment (3-4) was applied; (3-1) denotes a group to which a (acetone: olive oil=3:1) solution was applied instead of the DNFB solution; and (3-2) denotes a group (Comparative Example) treated in the same way as in (3-3) except that an ointment containing the GPIGS [SEQ ID NO: 6] ointment (3-3) except for GPIGS [SEQ ID NO: 6] was applied thereto.

In this context, the amount of water evaporation of (3-2) was 8.42 g/m$^2$/hr and was significantly larger than that of (3-1) (1.83 g/m$^2$/hr). This could demonstrate that the barrier function of keratin was remarkably reduced in the mouse skin to which the DNFB solution was applied, as in Example 1. The amounts of water evaporation of (3-3) (the present invention) and (3-4) (the present invention) were 5.23 g/m$^2$/hr and 3.89 g/m$^2$/hr, respectively, and were significantly lower than that of (3-2) (Comparative Example). This demonstrated that GPIGS [SEQ ID NO: 6] exhibited an improving effect on the barrier function of keratin damaged by dermatitis. As is evident from the comparison between (3-3) and (3-4), a concentration-dependent improving effect on the barrier function of keratin was observed, and this effect was more effective at the concentration of 3 mg/ml.

Example 6

The same experiment as in Example 1 was conducted except that isoleucylglycylserine (hereinafter, also referred to as "IGS") was used instead of GPIGS [SEQ ID NO: 6] to prepare 1 mg/ml IGS solution (6). As a result, IGS also exhibited, as with GPIGS [SEQ ID NO: 6] an improving effect on the barrier function of keratin damaged by dermatitis, as shown in FIG. 4.

Figure 4:
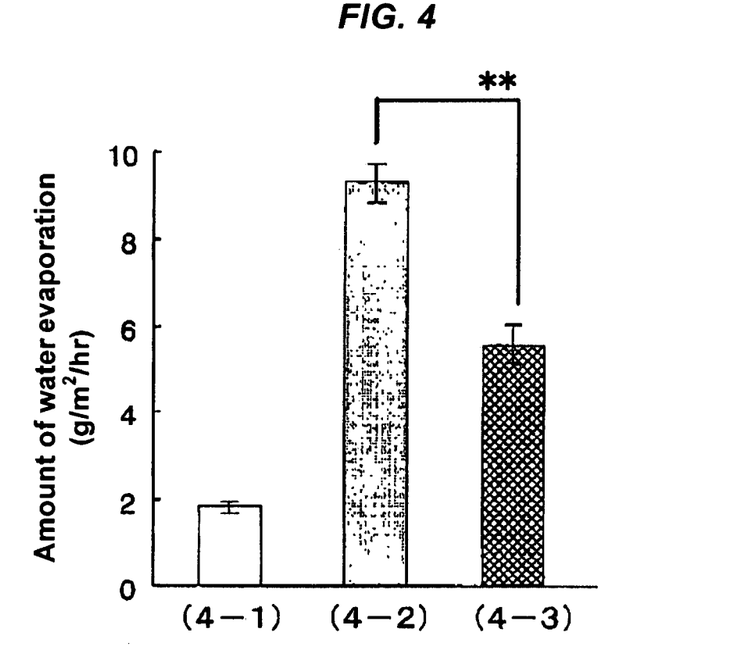
FIG. 4 is a graph showing an amount of water evaporation when a solution of a tripeptide is applied to inflammatory skin.

In FIG. 4, (4-3) denotes a group (the present invention) to which 1 mg/ml IGS solution (6) was applied; (4-1) denotes a group to which a (acetone:olive oil=3:1) solution was applied instead of the DNFB solution; and (4-2) denotes a group (Comparative Example) treated in the same way as in (4-3) except that a solution containing the IGS solution except for IGS was applied thereto.

In this context, the amount of water evaporation of (4-2) was 9.29 g/m$^2$/hr and was significantly larger than that of (4-1) (1.83 g/m$^2$/hr). This could demonstrate that the barrier function of keratin was remarkably reduced in the mouse skin to which the DNFB solution was applied, as in Example 1. The amount of water evaporation of (4-3) (the present invention) was 5.57 g/m$^2$/hr and was significantly lower than that of (4-2) (Comparative Example). This demonstrated that GPIGS [SEQ ID NO: 6] exhibited an improving effect on the barrier function of keratin damaged by dermatitis.

Example 7

A 100 mg portion of Hiviswako 104 (manufactured by Wako Pure Chemical Industries, Ltd.), 7.8 ml of Otsuka distilled water for injection, 2 ml of ethanol, 50 μl of 1 N HC1, and 50 μl of 5 M NaOH were added to 10 mg of GPIGS [SEQ ID NO: 6] or IGS and mixed together to prepare GPIGS [SEQ ID NO: 6] and IGS ointments [(5-3) and (5-4) in this order]. These ointments were separately applied to mice treated in the same way as in Example 3. As a result, both of the GPIGS [SEQ ID NO: 6] ointment (5-3) and the IGS ointment (5-4) exhibited an improving effect on the barrier function of keratin damaged by UVB irradiation, as shown in FIG. 5.

Figure 5:
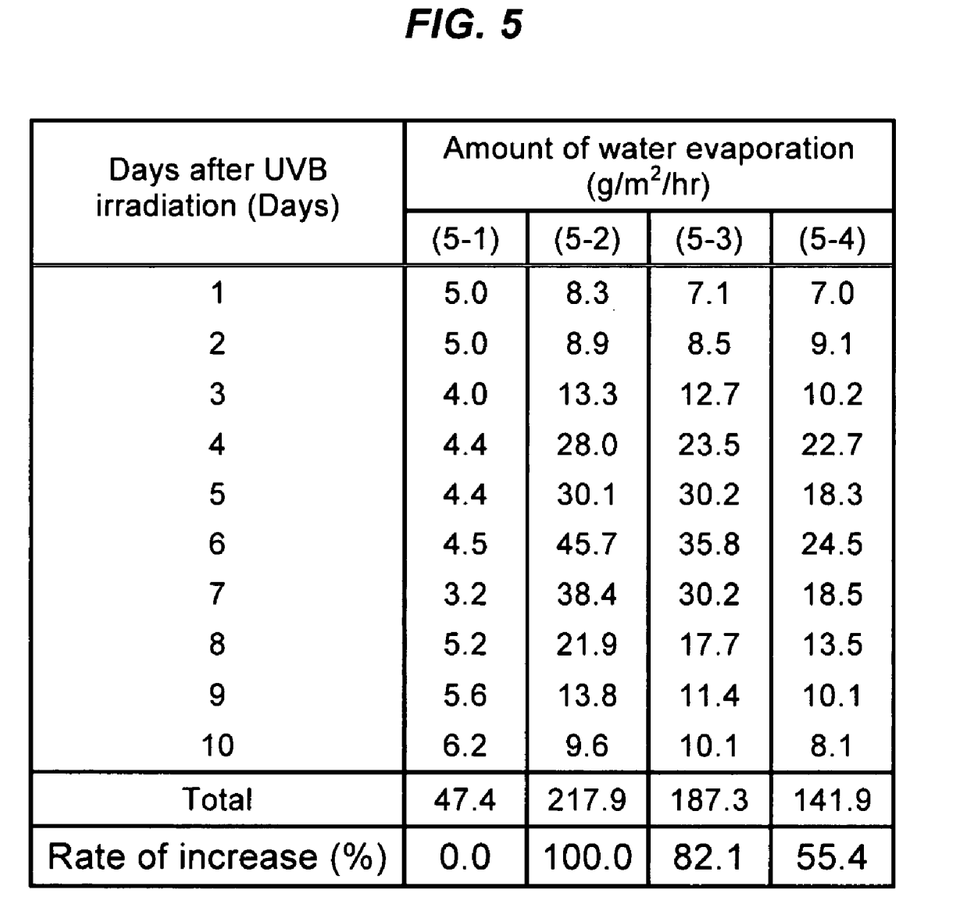
FIG. 5 is a graph showing an amount of water evaporation when ointments of a pentapeptide and a tripeptide are applied to UV-irradiated skin.

In FIG. 5, (5-3) denotes a group (the present invention) to which 1 mg/ml GPIGS [SEQ ID NO: 6] ointment was applied; (5-4) denotes a group (the present invention) to which 1 mg/ml IGS ointment was applied; (5-1) denotes a group without UVB irradiation; and (5-2) denotes a group (Comparative Example) treated in the same way as in (5-3) except that an ointment containing the GPIGS [SEQ ID NO: 6] ointment (5-3) except for GPIGS [SEQ ID NO: 6] was applied thereto.

All the amounts of water evaporation of (5-2) to (5-4) were increased due to continuous UVB irradiation as the day went on. However, the rate of this increase was lower in (5-3) (the present invention) and (5-4) (the present invention) than in (5-2) (Comparative Example). When the rate of increase in the total amount of water evaporation of (5-2) (Comparative Example) from the 1st day to the 10th day after UVB irradiation with respect to that of (5-1) is defined as 100%, the rates of increase of (5-3) (the present invention) and (5-4) (the present invention) were 82.1% and 55.4%, respectively, indicating evident inhibition. These results demonstrated that GPIGS [SEQ ID NO: 6] and IGS exhibited an improving effect on the barrier function of keratin damaged by UVB irradiation.

The invention claimed is:

1. A method for inhibition or therapeutic treatment of UV-induced dermatitis which comprises applying, to the surface of an affected skin of a patient, a medicament which comprises at least one member selected from the group consisting of: water-soluble peptides consisting of at least one unit selected from the group consisting of an isoleucylglycylseryl unit, a prolylisoleucylglycylseryl [SEQ ID NO: 2] unit, a glycylprolylisoleucylglycylseryl [SEQ ID NO: 6] unit, a glycylprolylisoleucylglycylthreonyl [SEQ ID NO: 7] unit and a glycylprolylisoleucylglycyl [SEQ ID NO: 1] unit; and water-soluble salts thereof.

2. The method of claim 1, wherein the medicament comprises at least one member selected from the group consisting of: water-soluble peptides consisting of at least one unit selected from the group consisting of an isoleucylglycylseryl unit and a glycylprolylisoleucylglycylseryl [SEQ ID NO: 6] unit; and water-soluble salts thereof.

3. The method of claim 1, wherein the medicament comprises at least one member selected from the group consisting of: water-soluble peptides consisting of an isoleucylglycylseryl unit; and water-soluble salts thereof.

4. The method of claim 1, wherein the medicament comprises at least one member selected from the group consisting of water-soluble peptides represented by the following Formula (1) and water-soluble salts thereof:

Gly-Pro-Ile-Gly-X[SEQ ID NO:8]   Formula (1)

wherein in the Formula (1), X is Ser or Thr.

5. The method of claim 1, wherein the water-soluble peptide is from 3 to 8 amino acids.

6. A method for inhibition or therapeutic treatment of atopic dermatitis which comprises applying, to the surface of an affected skin of a patient, a medicament which comprises at least one member selected from the group consisting of: water-soluble peptides consisting of at least one unit selected from the group consisting of an isoleucylglycylseryl unit, a prolylisoleucylglycylseryl [SEQ ID NO: 2] unit, a glycylprolylisoleucylglycylseryl [SEQ ID NO: 6] unit, a glycylprolylisoleucylglycylthreonyl [SEQ ID NO: 7] unit and a glycylprolylisoleucylglycyl [SEQ ID NO: 1] unit; and water-soluble salts thereof.

7. The method of claim 6, wherein the medicament is a solution comprising at least one member selected from the group consisting of water-soluble peptides represented by the following Formula (1) and water-soluble salts thereof in a concentration of 3 mg/ml or higher:

Gly-Pro-Ile-Gly-X[SEQ ID NO:8]   Formula (1)

wherein in the Formula (1), X is Ser or Thr.

8. The method according to claim 6 wherein the medicament is an ointment.

9. The method according to claim 6 wherein the medicament is in a solid form.

10. The method of claim 1, wherein the water-soluble peptide is isoleucylglycylserine.

11. The method of claim 6, wherein the water-soluble peptide is isoleucylglycylserine.

* * * * *